United States Patent
Martin et al.

(10) Patent No.: US 9,914,734 B2
(45) Date of Patent: Mar. 13, 2018

(54) CYCLIC ENERGETIC NITRAMINES DESENSITIZED WITH LINEAR NITRAMINES

(75) Inventors: James D. Martin, Mineral, VA (US); Edward O. Hosey, Culpeper, VA (US); Scott K. Dawley, Culpeper, VA (US)

(73) Assignee: AEROJET ROCKETOYNE, INC., Rancho Cordova, CA (US)

( * ) Notice: Subject to any disclaimer, the term of this patent is extended or adjusted under 35 U.S.C. 154(b) by 323 days.

(21) Appl. No.: 13/264,721

(22) PCT Filed: Apr. 14, 2010

(86) PCT No.: PCT/US2010/030993
§ 371 (c)(1),
(2), (4) Date: Jan. 25, 2012

(87) PCT Pub. No.: WO2010/120852
PCT Pub. Date: Oct. 21, 2010

(65) Prior Publication Data
US 2012/0111460 A1     May 10, 2012

Related U.S. Application Data

(60) Provisional application No. 61/169,902, filed on Apr. 16, 2009.

(51) Int. Cl.
| C06B 25/34 | (2006.01) |
| C07D 487/04 | (2006.01) |
| C07D 255/02 | (2006.01) |
| C07D 403/04 | (2006.01) |
| C07D 487/10 | (2006.01) |
| C06B 25/00 | (2006.01) |
| D03D 23/00 | (2006.01) |
| D03D 43/00 | (2006.01) |

(52) U.S. Cl.
CPC ............ *C07D 487/04* (2013.01); *C06B 25/34* (2013.01); *C07D 255/02* (2013.01); *C07D 403/04* (2013.01); *C07D 487/10* (2013.01)

(58) Field of Classification Search
USPC .............................. 149/92, 88, 109.2, 109.4
See application file for complete search history.

(56) References Cited

U.S. PATENT DOCUMENTS

| 4,961,380 | A | * | 10/1990 | Flanagan | ................. C06B 25/34 102/287 |
| 5,520,756 | A | * | 5/1996 | Zeigler | ................... C06B 25/18 149/19.7 |
| 5,520,757 | A | | 5/1996 | Lutz | |
| 5,574,240 | A | * | 11/1996 | Cartwright | ............. C06B 47/00 124/3 |
| 6,183,574 | B1 | | 2/2001 | Warren | |
| 2001/0044544 | A1 | | 11/2001 | Bottaro et al. | |
| 2005/0281968 | A1 | | 12/2005 | Shanholtz et al. | |

OTHER PUBLICATIONS

International Search Report dated Jun. 8, 2010 issued in related International Patent Application No. PCT/US2010/030993, filed Apr. 14, 2010.

* cited by examiner

*Primary Examiner* — James E McDonough
(74) *Attorney, Agent, or Firm* — Joel G Landau

(57) ABSTRACT

Propellant compositions containing cyclic nitramines that are susceptible to unintentional detonation are desensitized by the incorporation of a linear nitramine having a backbone containing one to three ethylene groups and one or two nitramine groups.

2 Claims, 2 Drawing Sheets

CYCLIC ENERGETIC NITRAMINES DESENSITIZED WITH LINEAR NITRAMINES

CROSS-REFERENCE TO RELATED APPLICATION

This application is the U.S. National Stage entry under § 371 of International Application No. PCT/US2010/030993, filed Apr. 14, 2010, which claims the benefit of United States Provisional Patent Application No. 61/169,902, filed Apr. 16, 2009 the contents of which are incorporated herein by reference.

BACKGROUND OF THE INVENTION

1. Field of the Invention

This invention relates to energetic compositions, and particularly to formulations to control the sensitivity of the compositions to shock.

2. Description of the Prior Art

The unintentional detonation of explosives and energetic compositions in general can result from a variety of causes and has led to catastrophes, both in military and industrial use. Prominent among the causes of unintentional detonation is the high sensitivity of these compositions to physical shock. A reduction of this sensitivity is needed for the safe processing of the explosives and also for achieving energetic compositions that can be classified under Class 1.3 ("mass fire") rather than Class 1.1 (mass detonable). Reduced sensitivity is also of value in the development of munitions that comply with the requirements for insensitive munitions (IM) and insensitive high explosives (IHE).

Among the formulations that have been developed to combine high performance with low sensitivity to meet IM and IHE standards are melt-cast and pour-castable explosives and explosives combined with polymeric binders. The usefulness of melt-cast and pour-castable compositions is limited, however, by various factors, one of which is the limited degree to which these compositions actually reduce the shock sensitivity of the explosives, and another is the loss of the desensitizing additives by sublimation at the elevated temperatures at which the rocket motors in which the explosives are used operate or at which they age, or both. This invention addresses these problems.

SUMMARY OF THE INVENTION

It has now been discovered that cyclic nitramines, which are prominent energetic compounds, can be successfully desensitized by linear nitramine additives without loss of energy. These additives have backbones containing one to three ethylene groups and one or two nitramine groups, with terminal groups that are either lower alkyl, nitrato ($O_2NO$—), or azido ($N_3$—), or other groups selected to achieve a melting point that is close to that of the primary explosive(s), i.e., the cyclic nitramine with which a particular linear nitramine is used. Among the various advantages offered by these linear nitramines are their high densities and their high decomposition temperatures.

DETAILED DESCRIPTION OF THE INVENTION AND PREFERRED EMBODIMENTS

Figure 1:
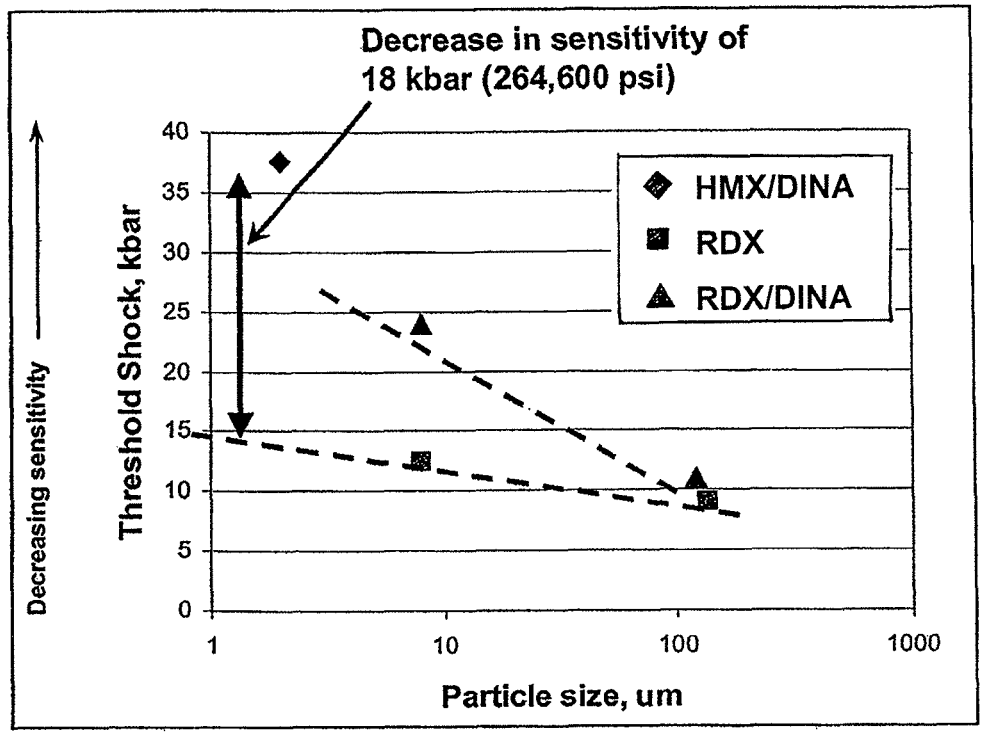
FIG. 1 is a plot of sensitivity vs. particle size for two compositions within the scope of this invention as well as one cyclic nitramine in the absence of a linear nitramine.

Examples of cyclic nitramines that can be desensitized by the present invention are those having the formula

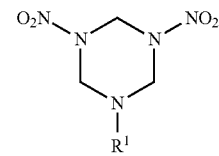

in which $R^1$ is either $NO_2$, $NO$, $C(O)CH_3$, $CH_2OCH_3$, $CH_2OC_2H_5$, $C_1$-$C_4$ alkyl, or cyclohexyl. A well-known example of a compound within this formula is that in which $R^1$ is $NO_2$, the compound being trimethylene trinitramine, commonly known as RDX or hexogen:

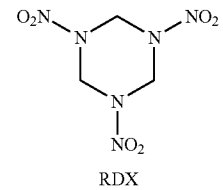

RDX

Another example is that in which $R^1$ is NO, the compound being 1,3-dinitro-5-nitroso-triazinane, of the formula

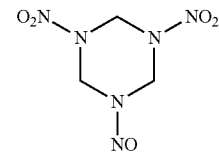

A further example, which is a variation on the above formula, is 1,3-dinitro-5-nitroso-triazinane, of the formula

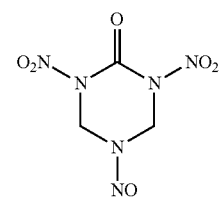

Further examples of cyclic nitramines that can be desensitized by the present invention are those having the formula

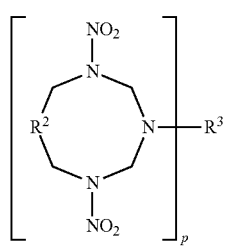

in which $R^2$ is either $CH_2$ or $N—R^4$, where $R^4$ is either $NO_2$, NO, $C(O)CH_3$, $CH_2OCH_3$, $CH_2OC_2H_5$, H, $C_1$-$C_4$ alkyl, or cyclohexyl; p is 1 or 2; and when p is 1, $R^3$ is either $NO_2$, NO, $C(O)CH_3$, $CH_2OCH_3$, $CH_2OC_2H_5$, H, $C_1$-$C_4$ alkyl, or cyclohexyl; and p 2, $R^3$ is $C_1$-$C_4$ alkylene, preferably $CH_2$.

A well-known example of a cyclic nitramine within this formula is one in which $R^2$ is $N—NO_2$, $R^3$ is $NO_2$, and p is 1. This compound is tetramethylene tetranitramine, commonly known as HMX or octogen, with the formula:

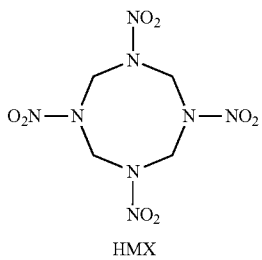

HMX

Further examples are:

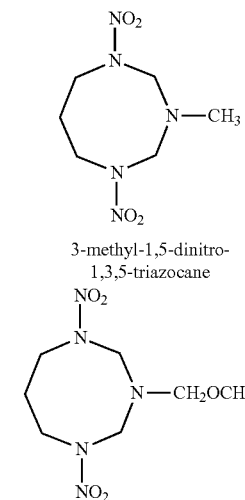

3-methyl-1,5-dinitro-
1,3,5-triazocane 3-isopropyl-1,5-dinitro-
1,3,5-triazocane

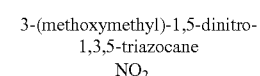

3-(methoxymethyl)-1,5-dinitro-
1,3,5-triazocane 1-(1,5-dinitro-1,3,5-triazocan-3-yl)-
ethanone

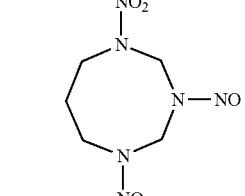

1,5-dinitro-3-nitroso-
1,3,5-triazocane 1,3,5-trinitro-1,3,5-triazocane

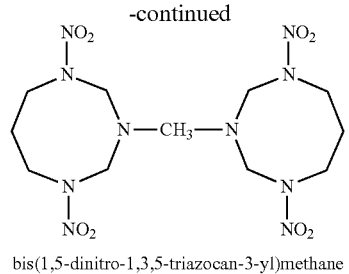

bis(1,5-dinitro-1,3,5-triazocan-3-yl)methane

A still further cyclic nitramine that can be desensitized by the present invention is 2,4,6,8,10,12-hexanitro-2,4,6,8,10,12-hexaazaisowurtzitane, commonly known as CL-20, having the formula

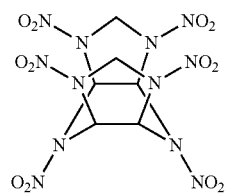 [SMILES: O=[N+]([O-])N1CN([N+](=O)[O-])C2C1N([N+](=O)[O-])C1C(N([N+](=O)[O-])CN1[N+](=O)[O-])N2[N+](=O)[O-]]

Still further cyclic nitramines that can be desensitized by the present invention are those of the formulae

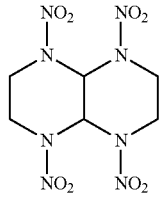 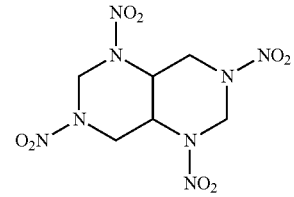

1,4,5,8-tetranitrodecahydro-
pyrazino[2,3-b]pyrazine 1,3,5,7-tetranitrodecahydro-
pyrimido[5,4-d]pyrimidine

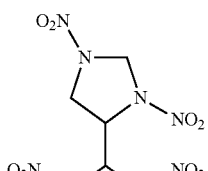 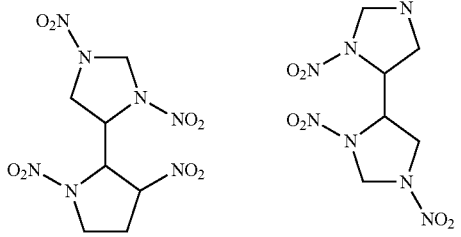

4-(1,3-dinitropyrrolidin-2-yl)-
1,3-dinitroimidazolidine 1,1',3,3'-tetranitro-
4,4'-biimidazolidine

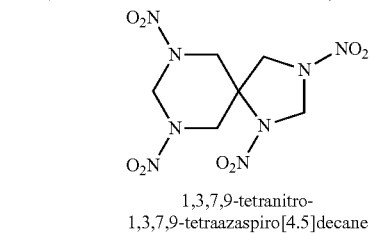

1,3,7,9-tetranitro-
1,3,7,9-tetraazaspiro[4.5]decane

Examples of linear nitramine desensitizing additives for use in the practice of this invention are those having the formula

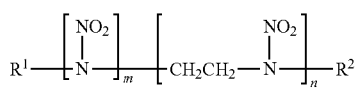

in which m is zero or 1; n is 1 or 2; $R^1$ is either $C_1$-$C_6$ alkyl, nitrato, azido, nitrato-$C_1$-$C_6$ alkyl, or azido-$C_1$-$C_6$ alkyl; and $R^2$ is either $C_1$-$C_6$ alkyl, nitrato, azido, nitrato-($C_1$-$C_6$ alkyl), or azido-($C_1$-$C_6$ alkyl); such that the total number of non-terminal $CH_2CH_2$ groups is one, two, or three, and the total number of nitrato groups is one or two. By "non-terminal $CH_2CH_2$ groups" is meant "not including $CH_2CH_3$ groups that occupy either the $R^1$ or $R^2$ positions." Preferred subclasses within this formula are those in which $R^1$ is either $C_1$-$C_3$ alkyl, nitrato, azido, nitrato-$C_1$-$C_3$ alkyl, or azido-$C_1$-$C_3$ alkyl, and $R^2$ is either $C_1$-$C_3$ alkyl, nitrato, azido, nitrato-($C_1$-$C_3$ alkyl), or azido-($C_1$-$C_3$ alkyl); and those in which $R^1$ is either $C_1$-$C_3$ alkyl, nitrato, azido, nitratoethyl, or azidoethyl, and $R^2$ is either $C_1$-$C_3$ alkyl, nitrato, azido, nitratoethyl), or azidoethyl. A further preferred subclass is that in which m is 1, n is 1, $R^1$ is either $C_1$-$C_6$ alkyl, nitrato, or azido, and $R^2$ is either $C_1$-$C_6$ alkyl, nitrato, or azido. A still further preferred subclass is that in which m is zero, n is 1, $R^1$ is either $C_1$-$C_6$ alkyl, nitrato, or azido, and $R^2$ is either $C_1$-$C_6$ alkyl, nitratoethyl, or azidoethyl. Yet another further preferred subclass is that in which m is 1, n is 1, $R^1$ is either $C_1$-$C_6$ alkyl, nitrato, or azido, and $R^2$ is either $C_1$-$C_6$ alkyl, nitrato, or azido. Preferred groups for $R^1$ and $R^2$ in general are methyl and ethyl.

Specific examples of linear nitramines within the above formula are dinitroxy diethyl nitramine (N,N-bis(2-nitroxyethyl)-nitramine or DINA), N,N'-2,5-dimethylethylene dinitramine (DMEDNA), N,N'-2,5-diethylethylene dinitramine (2,5-DNH), and N,N'-bis(2-nitratoethyl)ethylene dinitramine. The structures of these compounds are shown below:

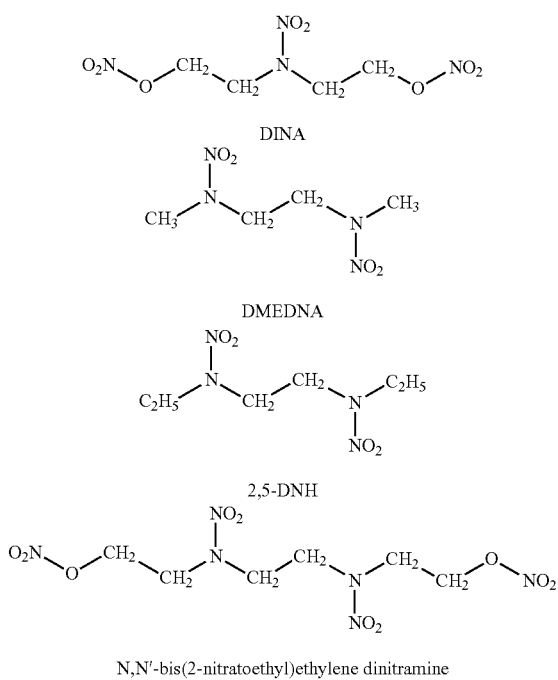

Other examples will be readily apparent to those skilled in the art. The selection of a particular linear nitramine is governed at least in part by its melting point or its sublimation point, which in preferred applications is within the range of 50° C. to 150° C., and also preferably no more than ten degrees Celsius below the melting point of the explosive. The formulation can contain a single linear nitramine desensitizer or two or more of the linear nitramines. Likewise, the formulation can contain a single cyclic nitramine explosive or two or more cyclic nitramine explosives. The weight ratio of the linear nitramine(s) to the cyclic nitramine(s) can vary, and is preferably within the range of from about 1:2 to about 2:1 (linear:cyclic).

EXAMPLES

Impact, friction sensitivity, and electrostatic discharge tests were performed on compositions both within and outside the scope of the invention, i.e., with and without a linear nitramine desensitized, using industry standard test procedures. Two linear nitramines, DINA and 2,5-DNH, were tested, using a 1:1 weight ratio of linear to cyclic in each case.

Results comparing HMX alone, RDX alone, and DINA with first HMX and then RDX are listed in Table I. In each case, the values shown are the lowest or most sensitive values from ten consecutive negative test results.

TABLE I

Comparison of Cyclic Nitramines With and Without Linear Nitramine Desensitizer Impact, Friction, and Electrostatic Discharge

| Test | HMX | HMX + DINA | RDX | RDX + DINA |
|---|---|---|---|---|
| Impact, kg-cm | 90 | 300 | 49 | 270 |
| Friction, psi @ drop angle | 500 @ 90° | 1800 @ 90° | 1200 @ 90° | 1400 @ 90° |
| Electrostatic Discharge, J @ 5 kv | 0.19 | 6 | 0.38 | 6 |

The results in Table I show consistent improvements due to the incorporation of the linear nitramine. The impact test result for the HMX/DINA formulation was at or near the maximum of the test instrument, which is 300 kg-cm. The friction test result for the HMX/DINA formulation was also at or near the maximum of the test instrument, while the friction test result for the RDX/DINA formulation was 200 psi greater than that observed for RDX alone. The electrostatic discharge test results for both desensitized materials were at the maximum value of the test instrument, where they were in the "green" region (normal handling conditions permitted), as compared to the "yellow" region (special handling required) for both HMX alone and RDX alone.

The HMX/DINA and RDX/DINA combinations were also subjected to small scale gap testing according to standard industry procedures, as was RDX alone for comparison. Such testing is commonly used to evaluate the shock sensitivity of solid energetic materials. The test procedure involves pressing the test material into a brass donor tube to within 98% of theoretical maximum density, the donor tube measuring 1.0 in. outer diameter, 0.2 in. inner diameter, and 1.5 in. length, over a brass acceptor tube of the same dimensions and a steel dent block measuring 3.0 in. diameter and 1.5 in. thickness, using a charge of 1.56 g/cm³ of the test material, a no. 6 detonator, and PMMA as the attenuator. All nitramine combinations were prepared by mixing the nitramines in melt form, then grinding the solidified mixtures to the desired particle size. The test was conducted with different particle sizes for both the RDX (squares) and the RDX/DINA combination (triangles), and with a single particle size (approximately 2 microns) for the HMX/DINA combination (diamond). The results in terms of threshold shock (initiation pressure) vs. particle size are shown in FIG. 1, which shows that the particle size affects the shock sensitivity. The results also validated the calibration results of 10-15 kbar obtained for RDX with a particle size near two microns. Significantly, the results extrapolated to the two-micron particle size show that the threshold shock required to initiate both the RDX/DINA combination and the HMX/DINA combination was significantly greater than the threshold shock for the RDX in the two-micron range. The decrease in sensitivity at this particle size was 18 kbar (264,600 psi).

Card gap tests were performed on a propellant formulation that contained the HMX/DINA combination and on one that contained HMX alone. Both formulations were 89% solids HTPB (hydroxyl-terminated polybutadiene) propellant formulations with two-micron particle-size propellants. (All percents herein are by weight unless otherwise stated.) The test was a Large Scale NOL (Naval Ordnance Laboratory) Gap Test. The propellant made with HMX/DINA was tested in Modified IHE (Insensitive High Explosive) Gap Tubes for preservation of the material. The results are shown in Table II below, which demonstrates that the substitution of HMX/DINA for HMX alone reduced the shock sensitivity of the propellant formulation by approximately 50%. The propellant made with standard HMX gave a positive test response at 85 cards and a negative test response at 89 cards. The propellant made with the HMX/DINA combination have a positive test response at 40 cards and a negative test response at 45 cards.

TABLE II

Comparison of Cyclic Nitramines With and Without Linear Nitramine Desensitizer Card Gap Tests

| Component | Weight Percent | |
|---|---|---|
| | Control | Invention |
| Binder | 11 | 11 |
| Aluminum | 19 | 19 |
| Ammonium perchlorate | 46 | 46 |
| HMX | 24 | — |
| HMX/DINA | — | 24 |
| Total: | 100 | 100 |

| Card Gap Test Results | Number of Cards | |
|---|---|---|
| Positive | 85 | 40 |
| Negative | 89 | 45 |

Figure 2:
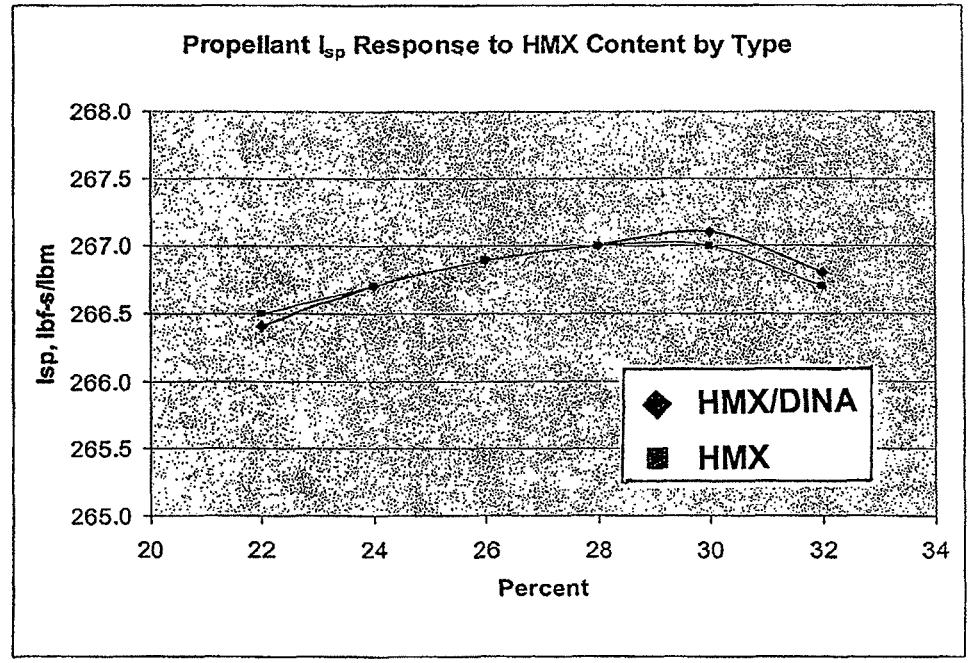
FIG. 2 is a plot of specific impulse for both a composition within the scope of this invention and the cyclic nitramine of the composition in the absence of the linear nitramine.

Theoretical performance (specific impulse) calculations were performed for both HMX and the HMX/DINA combination, over a range of 22-32% of each propellant formulations at the expense of ammonium perchlorate. The results are shown in FIG. 2 (the diamonds representing the HMX/DNA combination and the squares representing HMX alone) which shows that the calculated results for the propellant containing the HMX/DINA combination were very close to those calculated for the standard HMX.

Figure 3:
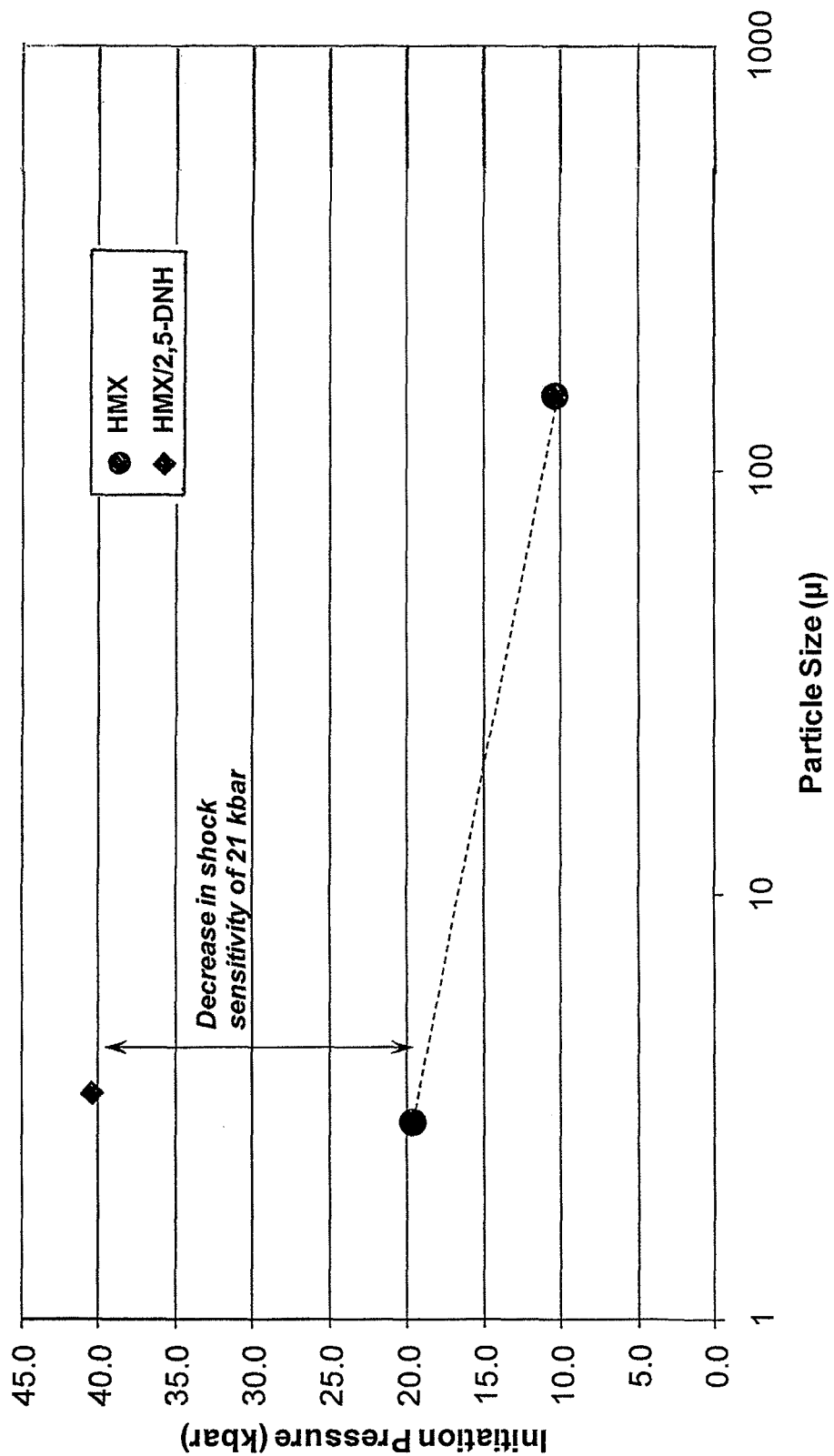
FIG. 3 is a plot of sensitivity vs. particle size for further compositions within the scope of this invention as well as one cyclic nitramine in the absence of a linear nitramine.

The effectiveness of 2,5-DNH was demonstrated, using HMX as the cyclic nitramine. Small scale gap tests using the same procedures as described above were run, and the results in terms of initiation pressure vs. particle size are shown in FIG. 3, where the circles represent the data obtained with HMX alone and the diamond represents the HMX/2,5-DNH combination. The data show a decrease in shock sensitivity of 21 kbar (308,700 psi) at the five-micron particle size due to the inclusion of the linear nitramine.

In the claim or claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:
1. A low-sensitivity propellant formulation comprising a cyclic nitramine and a linear nitramine, wherein said linear nitramine is a solid energetic material having a melting point within a range of 50° C. to 150° C. and has the formula

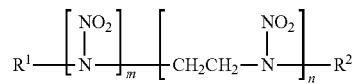

wherein:
m is zero or 1;
n is 1 or 2;
$R^1$ is a member selected from the group consisting of $C_1$-$C_6$ alkyl, nitrato, azido, nitrato-$C_1$-$C_6$ alkyl, and azido-$C_1$-$C_6$ alkyl; and
$R^2$ is a member selected from the group consisting of $C_1$-$C_6$ alkyl, nitrato, azido, nitrato-($C_1$-$C_6$ alkyl) and azido-($C_1$-$C_6$ alkyl);
such that the total number of non-terminal $CH_2CH_2$ groups is one, two, or three, and the total number of nitrato groups is one or two; and
wherein said cyclic nitramine has the formula

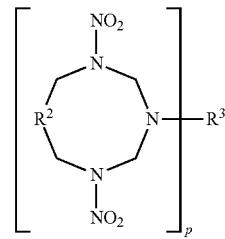

wherein:
$R^2$ is a member selected from the group consisting of $CH_2$ and N—$R^4$ in which $R^4$ is a member selected from the group consisting of $NO_2$, NO, $C(O)CH_3$, $CH_2OCH_3$, $CH_2OC_2H_5$, H, $C_1$-$C_4$ alkyl, and cyclohexyl;
P is 1 or 2; and
when p is 1, $R^3$ is a member selected from the group consisting of $NO_2$, NO, $C(O)CH_3$, $CH_2OCH_3$, $CH_2OC_2H_5$, H, $C_1$-$C_4$ alkyl, and cyclohexyl, and when p is 2, $R^3$ is $C_1$-$C_4$ alkylene, wherein said liner nitramine is N,N'-2,5-diethylethylene dinitramine.

2. A low-sensitivity propellant formulation comprising:

a cyclic nitramine and a linear nitramine, wherein said linear nitramine is a solid energetic material having a melting point within a range of 50° C. to 150° C. and has the formula

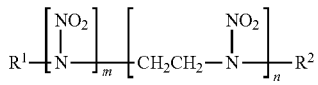

wherein:

m is zero or 1; n is 1 or 2;

$R^1$ is a member selected from the group consisting of $C_1$-$C_6$ alkyl, nitrato, and azido; and $R^2$ is a member selected from the group consisting of $C_1$-$C_6$ alkyl, nitrato, and azido, such that the total number of non-terminal $CH_2CH_2$ groups is one, two, or three, and the total number of nitrato groups is one or two; and wherein said cyclic nitramine has the formula

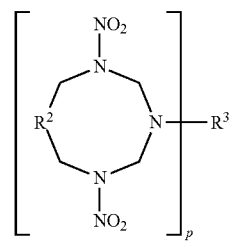

wherein:

$R^2$ is a member selected from the group consisting of $CH_2$ and N—$R^4$ in which $R^4$ is a member selected from the group consisting of $NO_2$, NO, $C(O)CH_3$, $CH_2OCH_3$, $CH_2OC_2H_5$, H, $C_1$-$C_4$ alkyl, and cyclohexyl;

P is 1 or 2; and when p is 1, $R^3$ is a member selected from the group consisting of $NO_2$, NO, $C(O)CH_3$, $CH_2OCH_3$, $CH_2OC_2H_5$H, $C_1$-$C_4$ alkyl, and cyclohexyl, and when p is 2, $R^3$ is $C_1$-$C_4$ alkylene.

* * * * *